United States Patent
Michels et al.

(10) Patent No.: US 7,546,166 B2
(45) Date of Patent: Jun. 9, 2009

(54) MEDICAL LEAD DESIGNS FOR LEAD PLACEMENT THROUGH TISSUE

(75) Inventors: Koen Michels, Maastricht (NL); Nicolaas M. Lokhoff, Kerkrade (NL)

(73) Assignee: Medtronic, Inc., Minneapolis, MN (US)

( * ) Notice: Subject to any disclaimer, the term of this patent is extended or adjusted under 35 U.S.C. 154(b) by 506 days.

(21) Appl. No.: 10/422,082

(22) Filed: Apr. 23, 2003

(65) Prior Publication Data

US 2004/0215307 A1 Oct. 28, 2004

Related U.S. Application Data

(63) Continuation-in-part of application No. 10/360,765, filed on Nov. 29, 2001, now abandoned.

(51) Int. Cl.
*A61N 1/05* (2006.01)
(52) U.S. Cl. .................. 607/125; 607/122; 607/126
(58) Field of Classification Search .......... 607/122, 607/125–130
See application file for complete search history.

(56) References Cited

U.S. PATENT DOCUMENTS

| | | | |
|---|---|---|---|
| 3,485,247 A | 12/1969 | Ackerman | 128/418 |
| 3,516,412 A | 6/1970 | Ackerman | 128/418 |
| 3,729,008 A | 4/1973 | Berkovits | |
| 3,857,399 A | 12/1974 | Zacouto | |
| 3,939,843 A | 2/1976 | Smyth | 128/404 |
| 4,033,357 A | 7/1977 | Helland et al. | |
| 4,332,259 A | 6/1982 | McCorkle, Jr. | |
| 4,402,328 A | 9/1983 | Doring | 128/785 |
| 4,475,560 A | 10/1984 | Tarjan et al. | |
| 4,928,688 A | 5/1990 | Mower | |
| 4,991,578 A * | 2/1991 | Cohen | 607/2 |
| 4,997,431 A | 3/1991 | Isner et al. | |
| 5,300,107 A * | 4/1994 | Stokes et al. | 607/126 |
| 5,330,496 A * | 7/1994 | Alferness | 606/171 |
| 5,374,287 A | 12/1994 | Rubin | |
| 5,383,922 A | 1/1995 | Zipes et al. | |
| 5,431,649 A | 7/1995 | Mulier et al. | |
| 5,628,778 A | 5/1997 | Kruse et al. | |
| 5,628,779 A | 5/1997 | Bornzin et al. | |
| 5,683,447 A | 11/1997 | Bush et al. | |
| 5,728,140 A | 3/1998 | Salo et al. | |
| 5,782,898 A | 7/1998 | Dahl et al. | |
| 5,964,795 A | 10/1999 | McVenes et al. | |
| 6,006,139 A | 12/1999 | Kruse et al. | |
| 6,055,457 A | 4/2000 | Bonner | |

(Continued)

OTHER PUBLICATIONS

U.S. Patent Application entitled, "Implantable Medical Lead Designs," U.S. Appl. No. 10/420,110, filed Apr. 21, 2003.

*Primary Examiner*—George R Evanisko
*Assistant Examiner*—Michael Kahelin
(74) *Attorney, Agent, or Firm*—Stephen W. Bauer

(57) ABSTRACT

The invention is directed to medical lead designs that facilitate implantation of the leads through tissue. For example, the leads can implanted though tissue for placement of distal tips of the leads in locations on the opposing side of the tissue. The leads include fixation elements, such as flexible tines, that facilitate fixation to the tissue. The fixation elements can protrude from lead at a location more than 5 millimeters from the distal-tip of the lead such that when the distal tip has passed through the tissue, the fixation elements anchor in the tissue.

9 Claims, 6 Drawing Sheets

U.S. PATENT DOCUMENTS

| | | |
|---|---|---|
| 6,144,882 A | 11/2000 | Sommer et al. |
| 6,201,994 B1 | 3/2001 | Warman et al. |
| 6,240,322 B1 * | 5/2001 | Peterfeso et al. ............ 607/126 |
| 6,321,123 B1 | 11/2001 | Morris et al. |
| 7,191,015 B2 * | 3/2007 | Lamson et al. .............. 607/119 |
| 2003/0199962 A1 * | 10/2003 | Struble et al. ............... 607/126 |

* cited by examiner

MEDICAL LEAD DESIGNS FOR LEAD PLACEMENT THROUGH TISSUE

This application is a continuation-in-part (CIP) of U.S. application Ser. No. 10/360,765, now abandoned entitled "Trans-septal medical electrical leads and methods of stimulating a heart" for Struble et al., which was originally filed as provisional U.S. Application Ser. No. 60/333,762, on Nov. 29, 2001 and was converted to a utility application on Nov. 28, 2002.

FIELD OF THE INVENTION

The invention relates to medical devices and, more particularly, to implantable medical leads for use with implantable medical devices (IMDs).

BACKGROUND OF THE INVENTION

In the medical field, implantable leads are used with a wide variety of medical devices. For example, implantable leads are commonly used to form part of implantable cardiac pacemaker systems that provide therapeutic stimulation to the heart by delivering pacing, cardioversion or defibrillation pulses. The pulses can be delivered to the heart via electrodes disposed on the leads, e.g., typically near distal ends of the leads. In that case, the leads can position the electrodes with respect to various cardiac locations so that the pacemaker can deliver pulses to the appropriate locations. Leads are also used for sensing purposes, or both sensing and stimulation purposes.

In addition, implantable leads are used with neurological devices such as deep-brain stimulation devices, and spinal cord stimulation devices. For example, leads can be stereotactically probed into the brain to position electrodes for deep brain stimulation. Leads are also used with a wide variety of other medical devices including, for example, devices that provide muscular stimulation therapy, devices that sense chemical conditions in a patient's blood, gastric system stimulators, implantable nerve stimulators, implantable lower colon stimulators, e.g., in graciloplasty applications, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, implantable hearing restoration devices, and the like. In short, medical leads can be used for sensing purposes, stimulation purposes, drug delivery, and the like.

A number of challenges exist with respect to medical leads. In particular, new and improved lead designs are often needed to facilitate medical implantation to specific locations within a patient. For example, as more advanced and complex pacing techniques are developed, it becomes desirable to facilitate lead implantation at new cardiac locations. Some recent advancements in pacing have made use of non-conventional locations for delivery of pacing pulses, such as left ventricular locations, atrial roof locations and epicardium locations to name a few. Other non-conventional locations for delivery of therapeutic pulses to the heart or other body locations will likely be discovered and used in the future.

BRIEF SUMMARY OF THE INVENTION

In general, the invention is directed to medical lead designs that facilitate implantation of the leads through tissue. For example, the leads can implanted though tissue for placement of distal electrodes of the leads in locations on the opposing side of the tissue. The leads include fixation elements, such as flexible tines, that facilitate fixation to the tissue. The fixation elements can protrude from the lead at a location more than 5 millimeters from the distal tip of the lead, such that when the distal tip has passed through the tissue, the fixation elements anchor in the tissue. In one example, the medical lead can be implanted through the inter-ventricular septum of a patient to access the left ventricle, with the fixation elements positioned in the inter-ventricular septum and the distal tip of the lead positioned adjacent the left ventricular wall.

In one embodiment, the invention provides a medical lead comprising a lead body that extends from a proximal end to a distal end, and a tissue fixation element protruding from the lead body at a location at least five millimeters from the distal end.

In another embodiment, the invention provides a system comprising an implantable medical device and an implantable lead. The lead includes a lead body that extends from a proximal end to a distal end, the proximal end being coupled to the implantable medical device. The lead also includes a tissue fixation element protruding from the lead body at a location at least five millimeters from the distal end.

In another embodiment, the invention provides a system comprising a catheter, a medical lead and a stylet. The catheter defines a proximal end and a distal end of the catheter and includes fixation structures on the distal end of the catheter for fixation to tissue. The medical lead can be inserted through the catheter and includes a lead body defining a lumen that extends from a proximal end to a distal end of the medical lead, and a tissue fixation element protruding from the lead body at a location at least five millimeters from the distal end of the medical lead. The stylet can be inserted through the lumen of the lead body, and a distal end of the stylet defines a piercing element for piercing tissue.

In another embodiment, the invention provides a method comprising attaching a distal end of a catheter to a right ventricular wall of a patient, inserting a stylet through a lumen of a medical lead to straighten a J-shaped distal region of the medical lead, the medical lead including a tissue fixation element protruding from the medical lead at a location at least five millimeters from the distal end of the medical lead, and inserting the stylet and medical lead through the catheter. The method also includes piercing an inter-ventricular septum with a distal end of the stylet, and inserting the distal end of the medical lead into a left ventricle of the patient through the inter-ventricular septum such that the tissue fixation element is positioned in the inter-ventricular septum.

DETAILED DESCRIPTION OF THE INVENTION

The invention is directed to medical lead designs that facilitate implantation of the leads through tissue. For example, the leads can implanted though tissue for placement of distal tips of the leads in locations on the opposing side of the tissue. An electrode can be disposed on the distal tip of the lead. In some embodiments, the distal region of the lead forms a J-shape for positioning of an electrode tip adjacent tissue once the lead is inserted through the tissue. In some embodiments, the leads include fixation elements, such as flexible tines, that facilitate fixation to the tissue.

For example, flexible tines can protrude from the lead at a location more than 5 millimeters from the distal tip of the lead such that the distal tip passes through the tissue and the flexible tines anchor in the tissue. In one example, described in greater detail below, the medical lead can be implanted through the inter-ventricular septum of a patient, with the fixation elements positioned in the inter-ventricular septum and a distal electrode tip positioned adjacent the left ventricular wall. In that case, the invention can facilitate left ventricular pacing and sensing without requiring lead implantation through the great vein. Instead, the lead is implanted through the right ventricle, through the inter-ventricular septum, and into the left ventricle. Many other applications of the lead features described herein may also exist.

Figure 1:
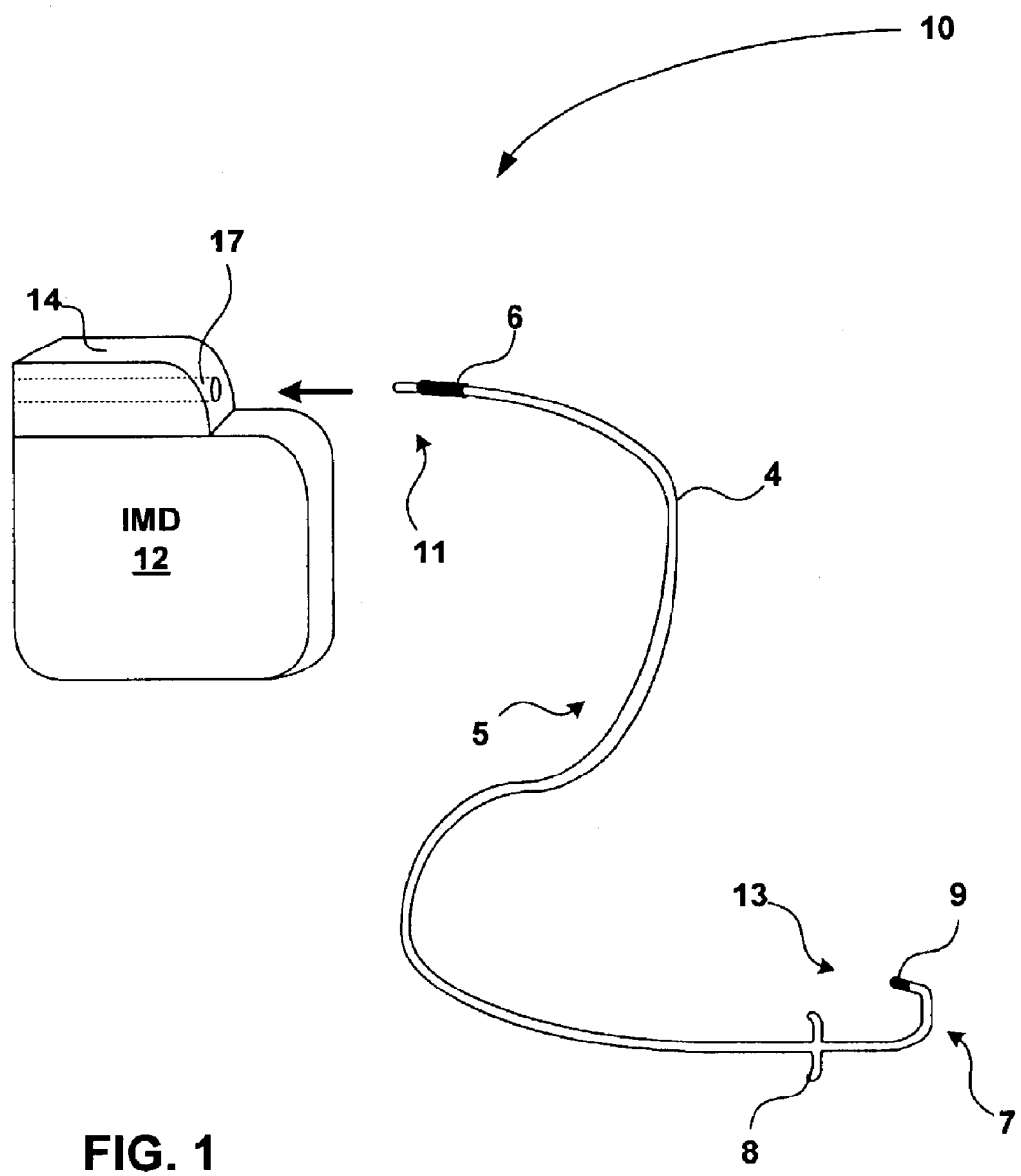
FIG. 1 is a perspective view of an exemplary implantable medical device system including an implantable medical device and an implantable medical lead according to an embodiment of the invention.

FIG. 1 is a perspective view of an exemplary implantable medical device system 10 for implantation in a human or other living being. In general, system 10 comprises an implantable medical device (IMD) 12, and an implantable medical lead 4 electrically coupled to IMD 12. In some cases, a plurality of additional leads can also be coupled to IMD 12. Implantable medical lead 4 defines a lead body 5 that extends from a proximal end 11 to a distal end 13. In general, implantable medical lead 4 positions electrode 9 within a patient so that therapeutic stimulation pulses can be delivered by IMD 12 to electrode 9 via lead 4. Additional leads and additional electrodes per lead can also be used.

In accordance with the invention, lead 4 includes one or more features that facilitate implantation of lead 4 through tissue for placement of electrode 9 on the opposing side of the tissue. For example, lead 4 defines a J-shaped distal region 7 which can allow placement of electrode 9 adjacent tissue following insertion of lead 4 through the tissue. In addition, implantable medical lead 4 includes one or more tissue fixation elements 8A, 8B, such as flexible tines which facilitate fixation of lead 4 within the tissue. These and other features described herein may be particularly useful for placement of electrode 9 adjacent a left ventricular wall of the patient's heart. In that case, fixation elements 8A, 8B can be positioned in the patient's inter-ventricular septum and J-shaped distal region 7 may reside in the patient's left ventricle.

Implantable medical lead 4 includes one or more electrodes, such as electrode 9 positioned on or near distal end 13 of implantable lead 4. In addition, any number of additional electrodes (not shown) may be distributed along the length of lead 4. Electrode 9 can be used for sensing, delivery of stimulation pulses, or possibly the delivery of high voltage shocks to a patient. Proximal end 11 of lead 4 includes an electrical contact element 6 which is electrically coupled to electrode 9 via one or more conductive elements that extend through lead body 5. For example, the conductive elements that extend through lead body 5 may comprise coiled filars that form a lumen through lead body 5. Proximal end 11 of lead 4 can be inserted into channel 17 of connector module 14 such that electrical contact element 6 is electrically coupled to circuitry within IMD 12. Connector module 14 forms part of IMD 12 and may be electrically coupled to sensing circuitry and/or stimulation circuitry within IMD 12.

Electrode 9 as well as other electrodes (if desired) can be made from an electrically conductive, biocompatible material such as elgiloy, platinum, platinum-iridium, platinum-iridium oxide, sintered platinum powder or other residue product after combustion with some high heat source, platinum coated with titanium-nitride, pyrolytic carbon, or the like. Although a single lead 4 is shown for purposes of illustration, any number of leads may be used, and thus coupled to connector module 14 of IMD 12. Lead 4 may comprise a bipolar lead that includes two electrodes, or may include any number of electrodes disposed along the body of lead 4.

In some embodiments, electrode 9 forms the distal most region of lead 4. Electrode 9 may form a substantially cylindrical ring of conductive material that extends about an exterior wall of lead 4. For example, electrode 9 can extend the entire 360 degrees about lead 4 or to some lesser extent. In some embodiments, lead 4 can be tubular but not necessarily cylindrical. For example, electrode 9 and lead 4 can have alternative cross sections, e.g., square, rectangular, hexagonal, oval or the like.

IMD system 10 may comprise any system that makes use of an IMD 12 and one or more implantable medical leads 4. For example, IMD 12 can take the form of an implantable cardiac pacemaker, cardioverter or defibrillator, or the like. In some embodiments, IMD 12 may be external (not implanted), with lead 4 forming an implantable portion of system 10. In most cases, however, IMD 12 and lead 4 are both implanted within a patient.

In the description that follows, many details of the invention will be provided in the context of a cardiac pacemaker system. In that case, IMD 12 takes the form of an implantable cardiac pacemaker that provides therapeutic stimulation to a patient's heart. In other embodiments, IMD 12 can take the form of an implantable cardioverter, an implantable defibrillator, or an implantable cardiac pacemaker-cardioverter-defibrillator (PCD). IMD 12 can deliver pacing, cardioversion or defibrillation pulses to a patient via various electrodes (not shown) disposed along the lead body 5 of lead 4. Accordingly, lead 4 positions one or more electrodes, including electrode 9, with respect to cardiac locations so that IMD 12 can deliver therapeutic pulses to the locations.

The invention, however, is not necessarily limited for use in pacemakers, cardioverters of defibrillators. Other uses of the leads described herein include uses in patient monitoring devices, or devices that integrate monitoring and stimulation features. In those cases, the leads can include sensors disposed on distal ends of the respective lead for sensing patient conditions.

Also, the leads described herein may find use with a neurological device such as a deep-brain stimulation device or a spinal cord stimulation device. In those cases, the leads can be stereotactically probed into the brain to position electrodes for deep brain stimulation, or into the spine for spinal stimulation. In other applications, the leads described herein can provide muscular stimulation therapy, gastric system stimulation, nerve stimulation, lower colon stimulation, drug or beneficial agent dispensing, recording or monitoring, gene therapy, or the like. In short, the leads described herein can find useful applications in a wide variety medical device systems. Specifically, the lead designs described in greater detail below can be very useful in applications where lead 4 is implanted through tissue for placement of electrode 9 adjacent the opposing side of the tissue.

Figure 2:
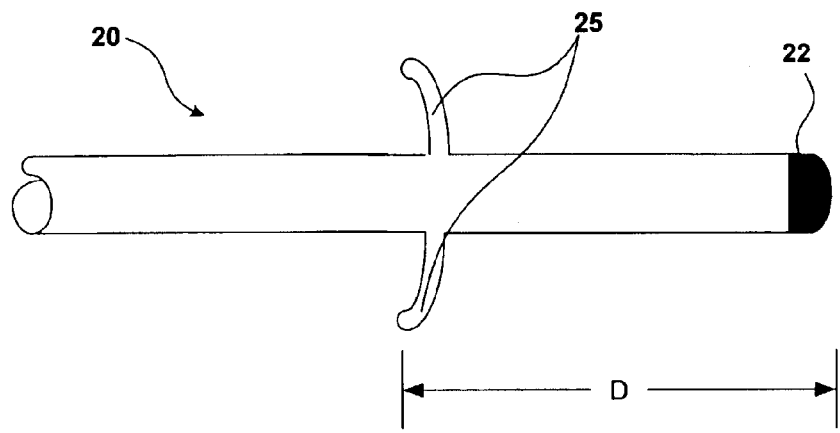
FIG. 2 is a cross-sectional side view of a distal region of an implantable medical lead according to an embodiment of the invention.

FIG. 2 is a cross-sectional side view of a distal region of lead 20 according to an embodiment of the invention. Lead 20 may correspond to lead 4 of FIG. 1. As shown in FIG. 2, lead 20 includes an electrode 22 disposed on the distal most tip of lead 20. Electrode 22 is electrically coupled to the proximal end (not shown) of lead 20 via one or more conductive elements that extend through the body of lead 20. For example, the conductive elements may comprise coiled filars that form a lumen through the body of lead 20.

In accordance with the invention, lead 20 includes one or more tissue fixation elements 25 that protrude from lead at a distance (D) more than 5 millimeters from the distal tip of lead 20. In this example, tissue fixation elements 25 comprise flexible tines that facilitate fixation of lead to tissue, e.g., via fibrous tissue growth. The tines may be hollow to promote such flexibility. In other examples, however, fixation elements 25 can comprise any of a wide variety of fixation structures, including for example, rings that extend radially outward from lead 20, rings that define holes for promoting fibrous growth of tissue with respect to the holes, an abrasive material that protrudes from lead 20, a saw-tooth structure that protrudes from lead 20, a beaded coating that protrudes from lead 20, spiral rings that protrude from lead 20, or the like.

By positioning fixation elements 25 at a distance (D) more than 5 millimeters from the distal tip of lead 20, electrode 22 can be positioned adjacent tissue on an opposing side of the tissue through which lead 20 is implanted. In accordance with the invention, the distance (D) may be between 5 and 35 millimeters, and more specifically between 10 and 20 millimeters. Such distances may be particularly useful for lead insertion through a patient's inter-ventricular septum for electrode placement in the left ventricle.

Figure 3:
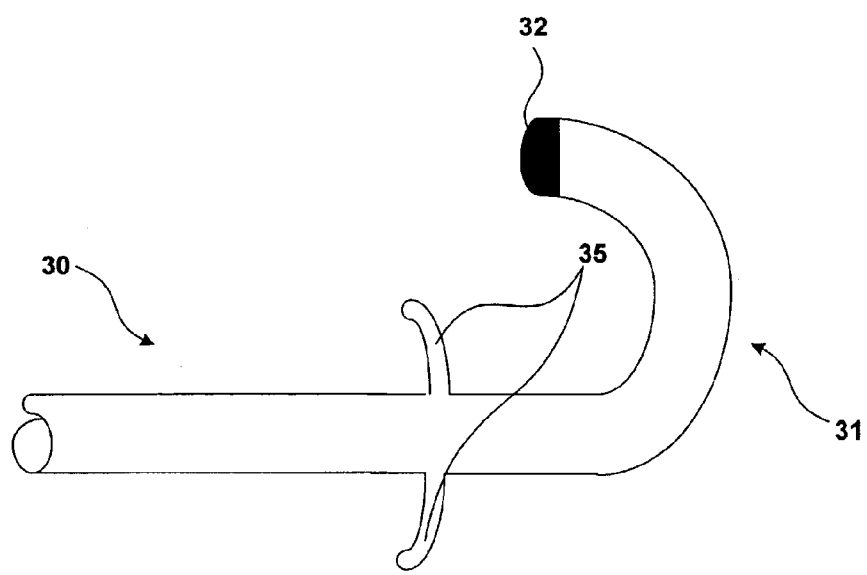
FIG. 3 is another cross-sectional side view of a distal region of an implantable medical lead according to an embodiment of the invention.

FIG. 3 is a cross-sectional side view of a distal region of lead 30, which is substantially similar to lead 20 of FIG. 2. One difference, however, is that lead 30 defines a J-shaped distal region 31. By way of example, the J-shaped distal region 31 may span a distal most 15-25 millimeters of the lead body. Electrode 32 is disposed on the distal most portion of J-shaped distal region 31. Tissue fixation elements 35 protrude from lead 30 at a distance more than 5 millimeters from the distal most tip of lead 30, e.g., more than 5 millimeters from electrode 32.

Lead 30 may be pre-shaped to define J-shaped distal region 31. Numerous techniques may be used to pre-shape the J-shaped distal region 31. In one example, heating and bending techniques can be used to shape end 31. In another example, the pitch of coiled filars can be adjusted and defined to form J-shaped distal region 31. The pitch refers to the lateral distance defined by one rotation of a filar. In another example, heating or molding of a polyurethane tubing (not shown) over J-shaped distal region 31 may be performed to create the J-shape in distal region 31 of lead 30. In another example, the conductive elements, e.g., coiled filars, may be formed of a memory metal that can be heated and shocked to create the J-shape. These or other shaping techniques can be used to form J-shaped distal region 31. In any case, the J-shape facilitates placement of electrode 32 adjacent tissue when fixation elements 35 are embedded in such tissue.

Figure 4:
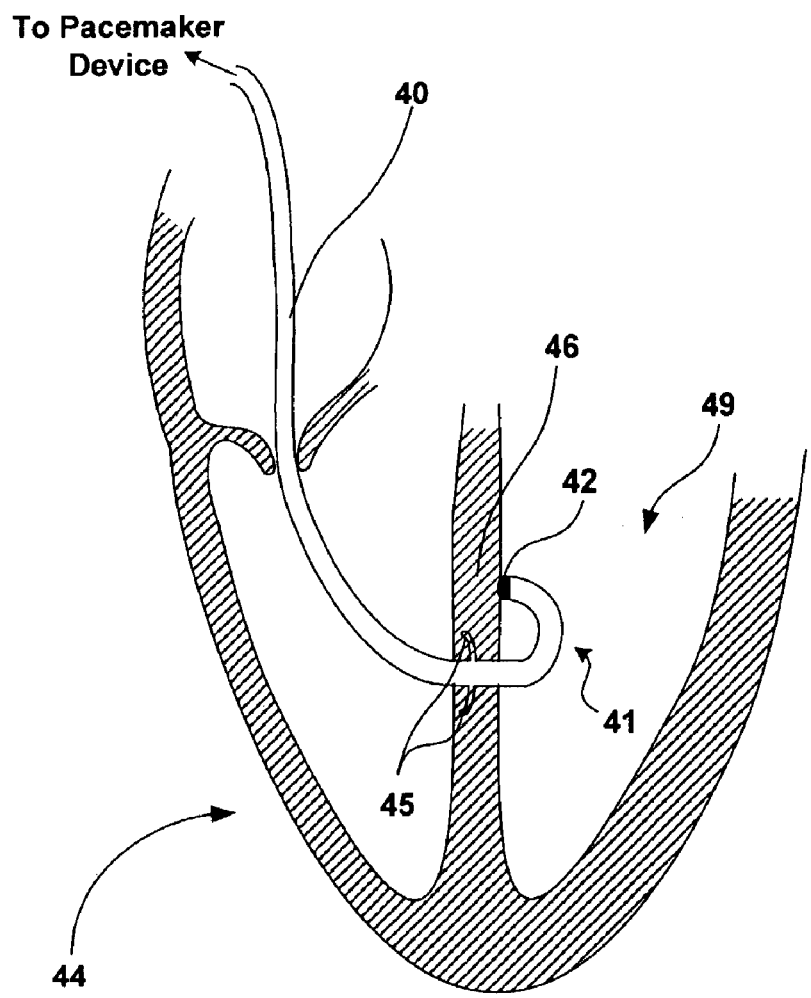
FIG. 4 is a cross-sectional view of a medical lead implanted in human heart according to an embodiment of the invention.

FIG. 4 is a cross-sectional view of a medical lead 40 implanted in human heart 44 according to an embodiment of the invention. In particular, lead 40 is implanted through the inter-ventricular septum 46 of heart 44. Fixation elements 45 of lead 40 are positioned within inter-ventricular septum 46 of heart 44 to secure lead 40 in place, e.g., by harnessing effects of fibrous tissue growth about fixation elements 45. J-shaped distal region 41 of lead 40 positions electrode 42 adjacent the wall of left ventricle 49. In this manner, the invention facilitates electrode placement in the left ventricle without requiring lead implantation through the great vein of the heart.

Figure 5:
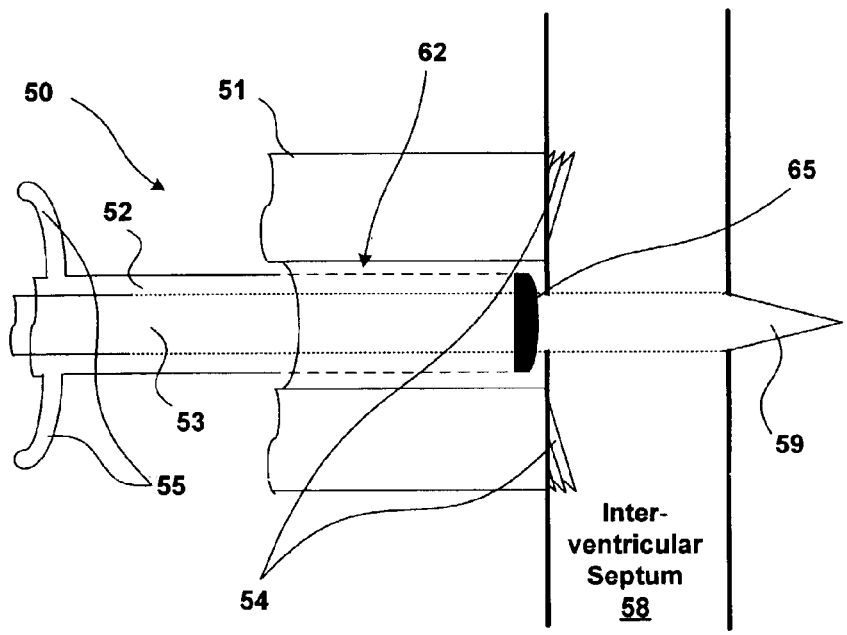
FIGS. 5-8 are conceptual cross-sectional side views illustrating a lead system that can be used for implantation of a medical lead through tissue such as the inter-ventricular septum of a patient's heart.
Figure 6:
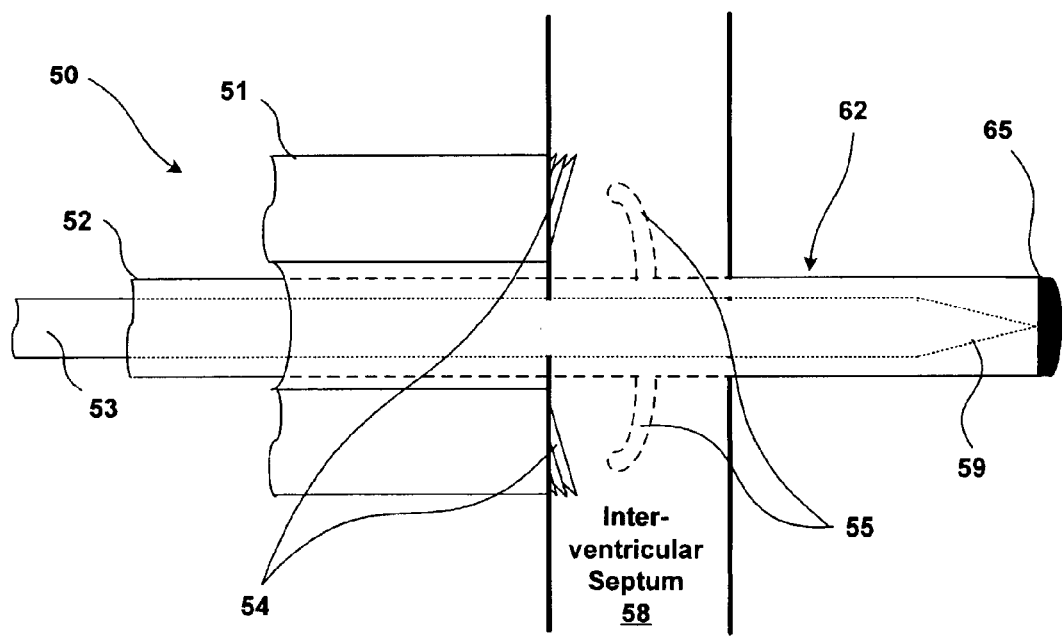
Figure 7:
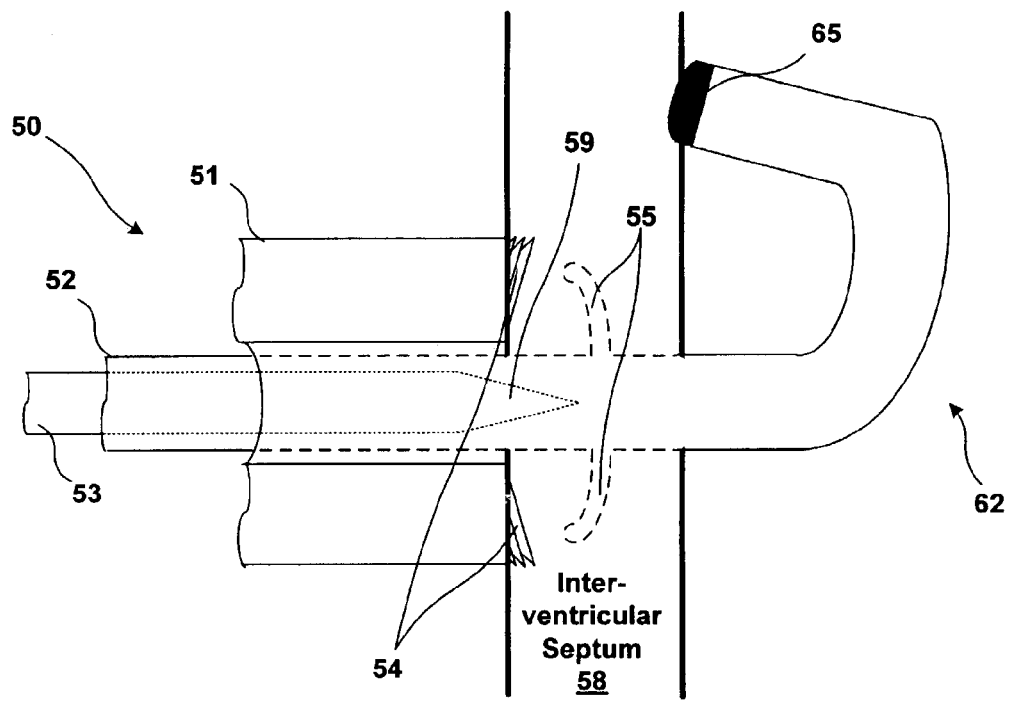

FIGS. 5-8 are conceptual cross-sectional side views illustrating a lead implantation system 50 that can be used for implantation of a medical lead 52 through tissue such as the inter-ventricular septum of the heart. The lead implantation system 50 includes a guiding catheter 51, a medical lead 52, and a stylet 53. As shown in FIGS. 5-7, guiding catheter 51 includes a fixation structure 54 on the distal end of guiding catheter 51 that can attach to tissue. In this example, fixation structure 54 of guiding catheter 51 is attached to the wall of the inter-ventricular septum 58, e.g., in the right atrium. Catheter 51, for example, can comprise a steerable catheter which the physician steers to the proper location in the patient's right ventricle adjacent the wall of inter-ventricular septum 58.

Figure 8:
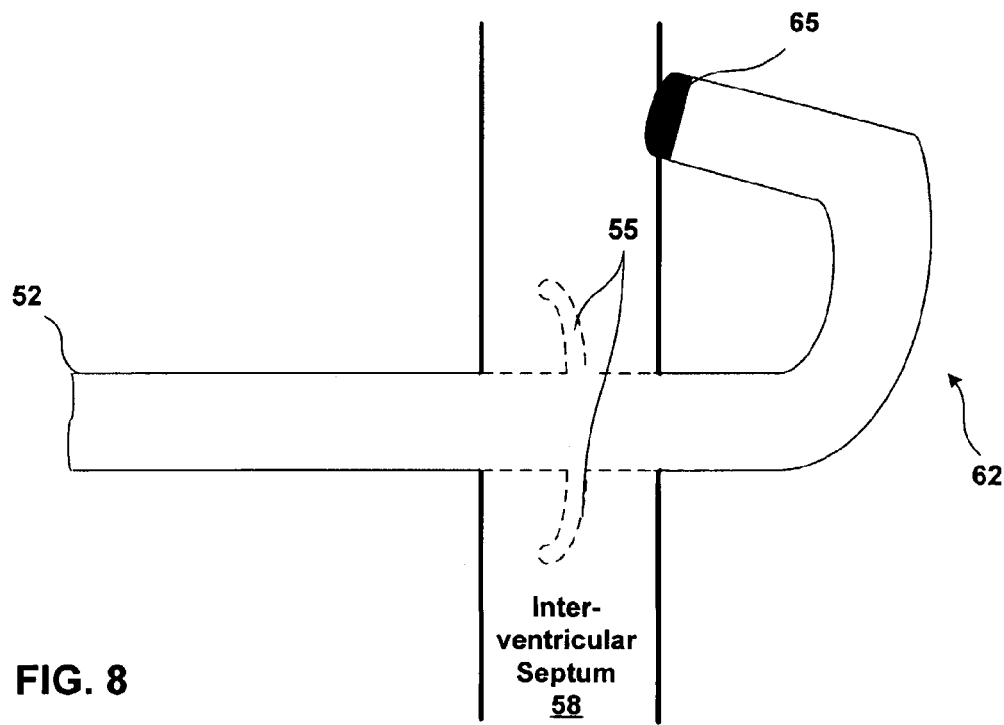

Medical lead 52 may define a pre-shaped distal region 62 that naturally assumes a J-shape as shown in FIGS. 7 and 8. However, during implantation, stylet 53 is inserted through a lumen of lead 52 causing distal region 62 of lead 52 to straighten as shown in FIGS. 5 and 6. Stylet 53 defines a piercing element 59, such as a sharpened tip, which is used to pierce the inter-ventricular septum 58 as shown in FIG. 5. If desired, fluid may be injected through catheter 51 and then detected by use of imaging techniques to determine whether stylet 53 has pierced inter-ventricular septum 58.

Next, lead 52 is inserted through the inter-ventricular septum 58 such that fixation elements 55 of lead 52 are positioned in the inter-ventricular septum 58, as shown in FIG. 6. Again, placement of fixation elements 55 in the inter-ventricular septum 58 can harness fibrous tissue growth to anchor lead 52 in place.

Once fixation elements 55 of lead 52 are positioned in the inter-ventricular septum 58, stylet 53 is withdrawn from the lumen of lead 52 as shown in FIG. 7. Upon withdrawal of stylet 53, the distal region 62 of lead 52 assumes its natural J-shape, causing positioning of electrode 65 adjacent the wall of inter-ventricular septum 58, e.g., in the left ventricle. Stylet 53 and catheter 51 can then be removed, leaving lead 52 properly implanted through inter-ventricular septum 58 such that electrode 65 is positioned adjacent the wall of inter-ventricular septum 58 for stimulation of the patient's left ventricle.

Figure 9:
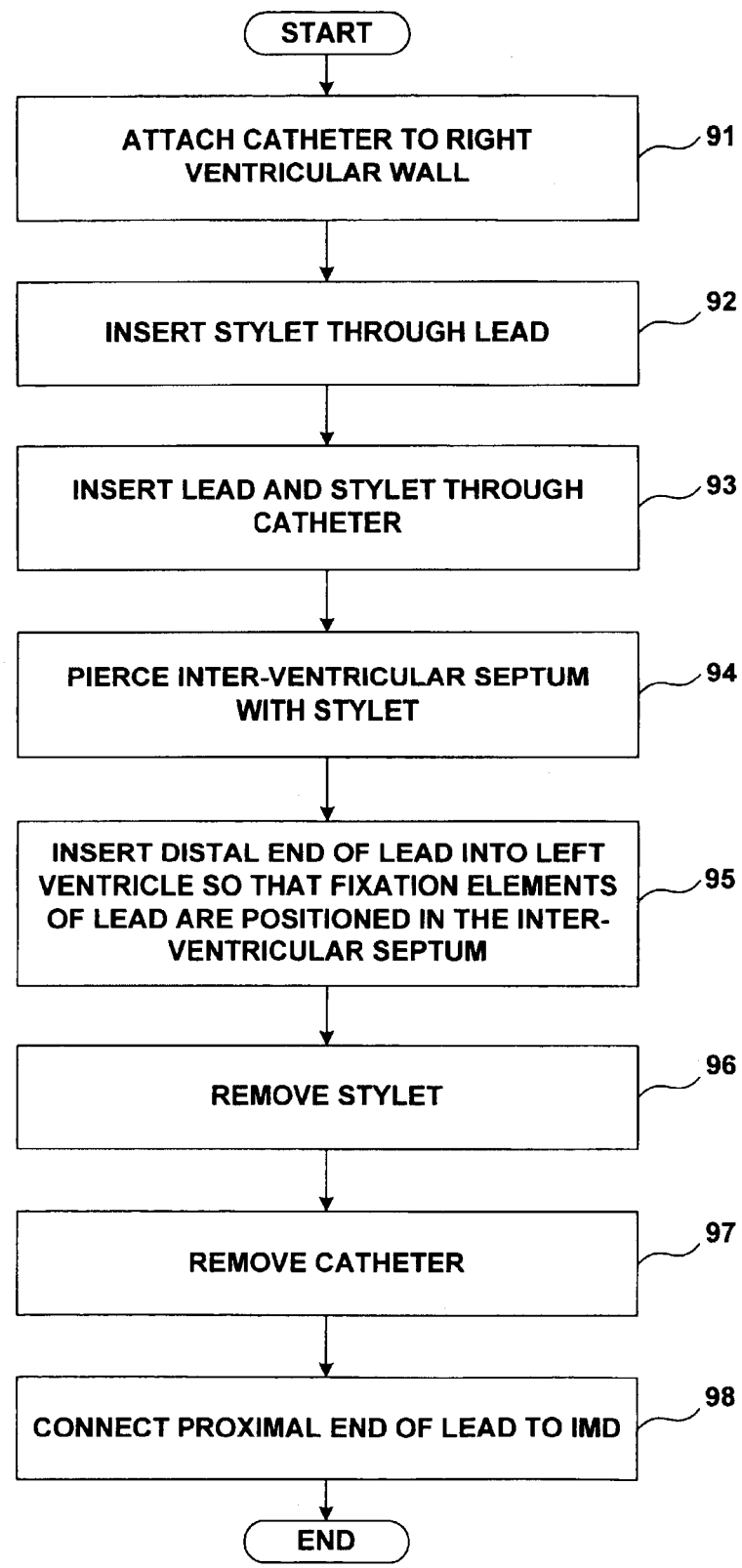
FIG. 9 is a flow diagram illustrating a procedure for implanting a medical lead through the inter-ventricular septum of a patient's heart such that an electrode of the lead is positioned adjacent the left ventricular wall for stimulation of the patient's left ventricle.

FIG. 9 is a flow diagram illustrating a procedure for implanting medical lead 51 through inter-ventricular septum 58 such that electrode 65 is positioned adjacent the wall of inter-ventricular septum 58 for stimulation of the patient's left ventricle. As shown in FIG. 9, catheter 51 is attached to the right ventricular wall (91), e.g., at inter-ventricular septum 58. Stylet 53 is inserted through lead 52 (92) causing J-shaped distal region 62 of lead 52 to straighten. Lead 52 and stylet 53 are inserted through catheter 51 (93).

Stylet 53 is used to pierce through inter-ventricular septum 58 (94), and if desired, a fluid may be injected through catheter and detected by use of imaging techniques to verify that stylet 53 has pierced all the way through inter-ventricular septum 58. Next, the distal region 62 of lead 52 is inserted into the left ventricle so that fixation elements 55 of lead 52 are positioned in inter-ventricular septum 58 (95).

Once lead 52 is properly positioned, stylet 53 is removed from the lumen of lead 52 (96), causing distal region 62 of lead 52 to assume its natural J-shape. Upon assuming its natural J-shape, the distal region 62 of lead 52 positions electrode 65 adjacent the left ventricular wall. Catheter 51 is then removed (97), and the proximal end of lead 52 is connected to an IMD (98), such as a cardiac pacemaker device. In this manner, lead 52 can be used to position electrode 65 adjacent the left ventricular wall to facilitate pacing of the left ventricle.

A number of embodiments of medical lead designs have been disclosed which can facilitate lead implantation through tissue. One skilled in the art will appreciate that the present invention can be practiced with embodiments other than those disclosed. For example, although many details of the invention have been described in the context of lead implantation through the inter-ventricular septum of the heart, the invention can find application in implantation in a wide variety of other locations, including other cardiac locations or other non-cardiac locations. For example, the leads described herein could be used to implant through the epicardium for implantation of an electrode on the myocardium, or through the myocardium for implantation of an electrode on the epicardium. Also, although fixation elements in the form of flexible tines have been specifically used to illustrate the invention, numerous other types of fixation elements could also be used. The disclosed embodiments are presented for purposes of illustration and not limitation, and the present invention is limited only by the claims that follow.

What is claimed is:

1. A medical lead, comprising:
   a lead body that extends from a proximal end to a distal end;
   a cardiac pacing electrode coupled to the distal end; and
   a pair of tissue fixation elements protruding from the lead body;
   wherein the pair of tissue fixation elements are adapted to be embedded within a volume of myocardial tissue to prevent migration of the lead within the myocardium and control the depth of the lead into the volume of myocardial tissue;
   wherein the volume of myocardial tissue comprises interventricular tissue;
   wherein the cardiac pacing electrode coupled to said distal end is adapted to contact the myocardium at a location spaced from the tissue fixation elements and a portion of the lead body distal to the tissue fixation elements is formed to have a J-shape;
   wherein a first of the pair of fixation elements protrudes from the lead body at a location between 10 and 20 millimeters from the distal end.

2. The medical lead of claim 1, wherein at least one of the pair of tissue fixation elements includes at least one flexible tine.

3. The medical lead of claim 2, wherein the tine comprises a hollow member.

4. The medical lead of claim 1, wherein the lead body is formed with a lumen adapted to permit passage of a stylet through said lumen.

5. The medical lead of claim 1, further comprising:
   an electrical contact element disposed near the proximal end of the lead body and electrically coupled to the electrode via one or more elongated conductive elements that extend a majority of the length of the lead body.

6. A system comprising:
   an implantable medical device; and
   an implantable lead including:
   a lead body that extends from a proximal end to a distal end, the proximal end being coupled to the implantable medical device;
   a cardiac pacing electrode operatively coupled to the distal end; and
   a pair of spaced apart tissue fixation elements with a first of the pair protruding from the lead body at a location spaced from the distal end of the lead body, wherein the pair of spaced apart tissue fixation elements are adapted to be embedded in a volume of myocardial tissue to prevent migration of the lead within the myocardium and control the depth of penetration of the lead into the myocardium and wherein said myocardium comprises interventricular tissue; and
   wherein the cardiac pacing electrode coupled to the distal end is adapted to contact the myocardium at a location spaced from the fixation elements and a portion of the lead body distal to the tissue fixation elements is formed to have a J-shape;
   wherein the first of the pair of fixation elements protrudes from the lead body at a location between 10 and 20 millimeters from the distal end.

7. The system of claim 6, wherein at least one of said pair of tissue fixation elements comprises a flexible tine.

8. The system of claim 7, wherein the tine comprises a hollow member.

9. The system of claim 6, the lead body further comprising an electrical contact element coupled near to the proximal end, the electrical contact element being electrically coupled to the implantable medical device and electrically coupled to the electrode via one or more elongated conductive elements.

* * * * *